United States Patent
Sueyasu

(10) Patent No.: US 10,271,717 B2
(45) Date of Patent: Apr. 30, 2019

(54) FLUID PLUG UNIT AND INSERTION DEVICE

(71) Applicant: OLYMPUS CORPORATION, Tokyo (JP)

(72) Inventor: Hidetada Sueyasu, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 63 days.

(21) Appl. No.: 15/370,406

(22) Filed: Dec. 6, 2016

(65) Prior Publication Data

US 2017/0079514 A1    Mar. 23, 2017

Related U.S. Application Data

(63) Continuation of application No. PCT/JP2015/066339, filed on Jun. 5, 2015.

(30) Foreign Application Priority Data

Jun. 13, 2014   (JP) .................. 2014-122797

(51) Int. Cl.
*A61B 1/00*   (2006.01)
*A61M 1/00*   (2006.01)
(Continued)

(52) U.S. Cl.
CPC .......... *A61B 1/015* (2013.01); *A61B 1/00068* (2013.01); *A61B 1/00094* (2013.01);
(Continued)

(58) Field of Classification Search
CPC . A61B 1/00094; A61B 1/00119; A61B 1/015; A61B 1/018; A61B 1/00068; A61M 39/22; A61M 39/23; A61M 2039/224
See application file for complete search history.

(56) References Cited

U.S. PATENT DOCUMENTS 3,903,877 A *  9/1975 Terada ............... A61B 1/00068
                                                        600/157
5,840,015 A    11/1998 Ogino
2006/0041190 A1  2/2006 Sato

FOREIGN PATENT DOCUMENTS

JP    2004-201866 A    7/2004
JP    2005-177210 A    7/2005
(Continued)

OTHER PUBLICATIONS

Extended Supplementary European Search Report dated Feb. 23, 2018 in European Patent Application No. 15 80 6717.3.
(Continued)

*Primary Examiner* — Aaron B Fairchild
(74) *Attorney, Agent, or Firm* — Scully, Scott, Murphy & Presser, P.C.

(57) ABSTRACT

A fluid plug unit includes a cylinder connected to a first conduit and a second conduit, and a piston configured execute switching between a first position where leakage of a fluid in the first conduit to an outside is suppressed, and a second position where the fluid is sucked. The fluid plug unit includes a first passage configured to communicate with the first conduit and the second conduit when the piston is disposed in the first position, and to shut off communication with the first conduit when the piston is disposed in the second position, and a second passage configured to shut off communication with the first conduit when the piston is disposed in the first position, and to communicate with the first conduit and the second conduit when the piston is disposed in the second position.

18 Claims, 8 Drawing Sheets

(51) Int. Cl.
  *A61B 1/015*   (2006.01)
  *A61B 1/018*   (2006.01)
  *A61B 17/29*   (2006.01)

(52) U.S. Cl.
  CPC ...... *A61B 1/00119* (2013.01); *A61B 1/00131* (2013.01); *A61B 1/018* (2013.01); *A61M 1/0035* (2014.02); *A61B 1/00087* (2013.01); *A61B 1/00177* (2013.01); *A61B 17/29* (2013.01)

(56)   References Cited

FOREIGN PATENT DOCUMENTS

| | | |
|---|---|---|
| JP | 2009-045130 A | 3/2009 |
| JP | 2010-268866 A | 12/2010 |
| JP | 2012-120664 A | 6/2012 |

OTHER PUBLICATIONS

International Preliminary Report on Patentability and Written Opinion dated Dec. 22, 2016 received in International Application No. PCT/JP2015/066339.
International Search Report dated Sep. 1, 2015 issued in PCT/JP2015/066339.
Japanese Office Action dated Mar. 15, 2016 issued in JP2015-559381.

* cited by examiner

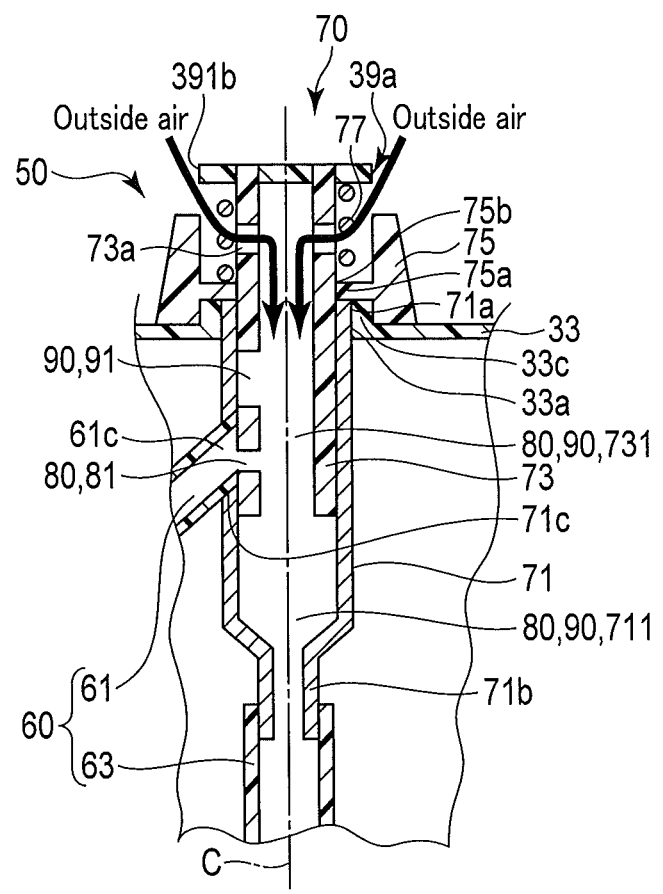
F I G. 2A

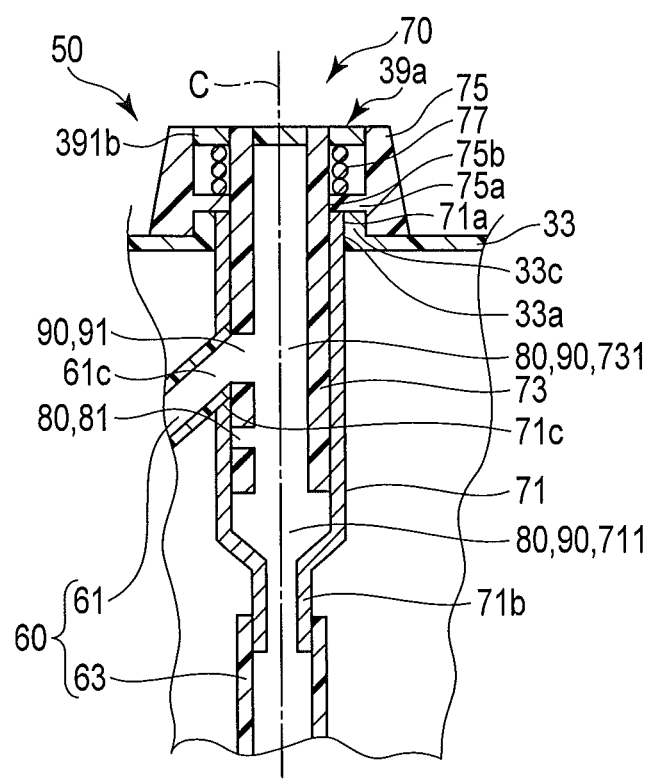
F I G. 2B

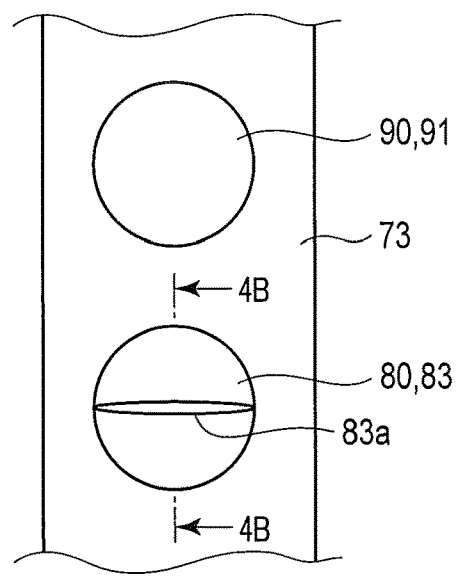
F I G. 4A
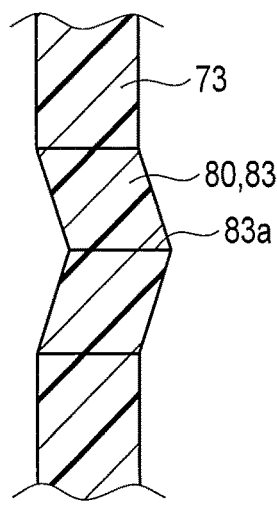
4B-4B
F I G. 4B 5B-5B

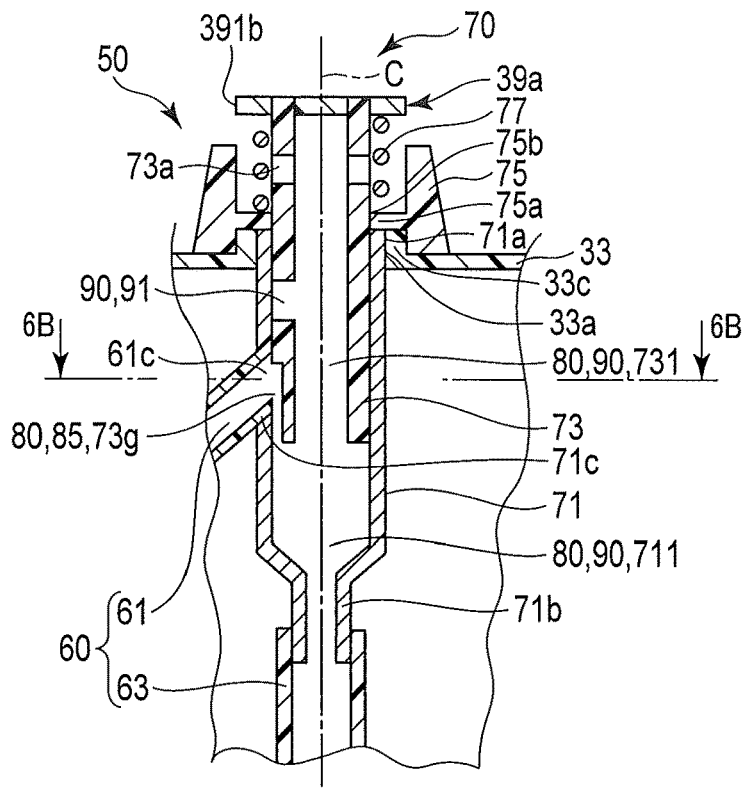
F I G. 6A
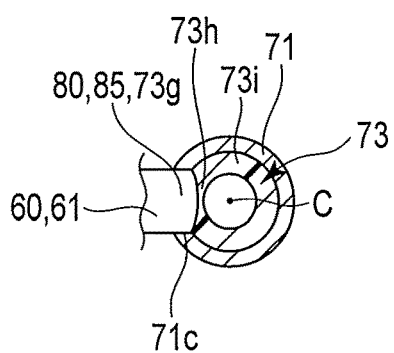
6B-6B
F I G. 6B

FLUID PLUG UNIT AND INSERTION DEVICE

CROSS-REFERENCE TO RELATED APPLICATIONS

This application is a Continuation application of PCT Application No. PCT/JP2015/066339, filed Jun. 5, 2015 and based upon and claiming the benefit of priority from prior Japanese Patent Application No. 2014-122797, filed Jun. 13, 2014, the entire contents of all of which are incorporated herein by reference.

BACKGROUND OF THE INVENTION

1. Field of the Invention

The present invention relates to a fluid plug unit and an insertion device.

2. Description of the Related Art

For example, an endoscope disclosed in, for example, Jpn. Pat. Appln. KOKAI Publication No. 2004-201866 is connected, via a connection portion provided in a universal cord of the endoscope, to a suction device provided on an outside of the endoscope, in order to suck fluids such as a body fluid including mucus and contaminated fluid in a lumen. This endoscope includes a fluid plug unit which switches one of a suction state and a non-suction state to the other, by a piston being pushed relative to a cylinder.

The endoscope further includes a suction conduit portion which includes a first suction conduit portion connected to the fluid plug unit, and a second suction conduit portion connected to the fluid plug unit.

The first suction conduit portion includes a distal end portion which is provided at a distal end portion of an endoscope insertion section, and proximal end portions which are two-forked at a proximal end portion of the endoscope insertion section. One part of the first suction conduit portion functions as a treatment instrument insertion channel which is provided from the distal end portion of the insertion section to a treatment instrument insertion portion that functions as one of the proximal end portions. The other part of the first suction conduit portion is provided from the two-forked portion to the fluid plug unit that functions as the other proximal end portion. The other part of the first suction conduit portion communicates with the one part of the first suction conduit portion at the two-forked portion.

The second suction conduit portion is provided from the fluid plug unit to the connection portion via the universal cord.

BRIEF SUMMARY OF THE INVENTION

An aspect according to a fluid plug unit of the invention is a fluid plug unit communicating with a first conduit including a distal end and a proximal end and configured to pass a fluid between the distal end and the proximal end, and communicating with a second conduit connected to a suction device and configured to pass the fluid, the fluid plug includes a cylinder connected to the first conduit and the second conduit such that the first conduit and the second conduit communicate with each other; a piston fittingly inserted into the cylinder and configured to move in an axial direction of the cylinder, thereby executing switching between a first position where leakage of the fluid in the first conduit to an outside is suppressed, and a second position where the fluid is sucked by the suction device via the first conduit and the second conduit; a first passage configured to communicate with the first conduit and the second conduit when the piston is disposed in the first position, and to shut off communication with the first conduit when the piston is disposed in the second position; and a second passage configured to shut off communication with the first conduit when the piston is disposed in the first position, and to communicate with the first conduit and the second conduit when the piston is disposed in the second position.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2A is a view for explaining a leakage suppression state in the first embodiment.

FIG. 2B is a view for explaining a suction state in the first embodiment.

FIG. 4A is a front view of a valve in a first modification of the first embodiment.

FIG. 4B is a cross-sectional view taken along line 4B-4B in FIG. 4A.

FIG. 6A is a view illustrating an example of the gap in the second embodiment.

FIG. 6B is a cross-sectional view taken along line 6B-6B in FIG. 6A.

DETAILED DESCRIPTION OF THE INVENTION

Embodiments of the present invention will be described hereinafter in detail with reference to the accompanying drawings.

First Embodiment

Configuration

A first embodiment will be described with reference to FIG. 1, FIG. 2A, FIG. 2B, FIG. 3A, FIG. 3B and FIG. 3C. Incidentally, in some of the drawings, depiction of some members is omitted for the purpose of clearer illustration, for example, like the omission of depiction of a cylinder 71 and a piston 73 in FIG. 1.

[Endoscope 10]

Figure 1:
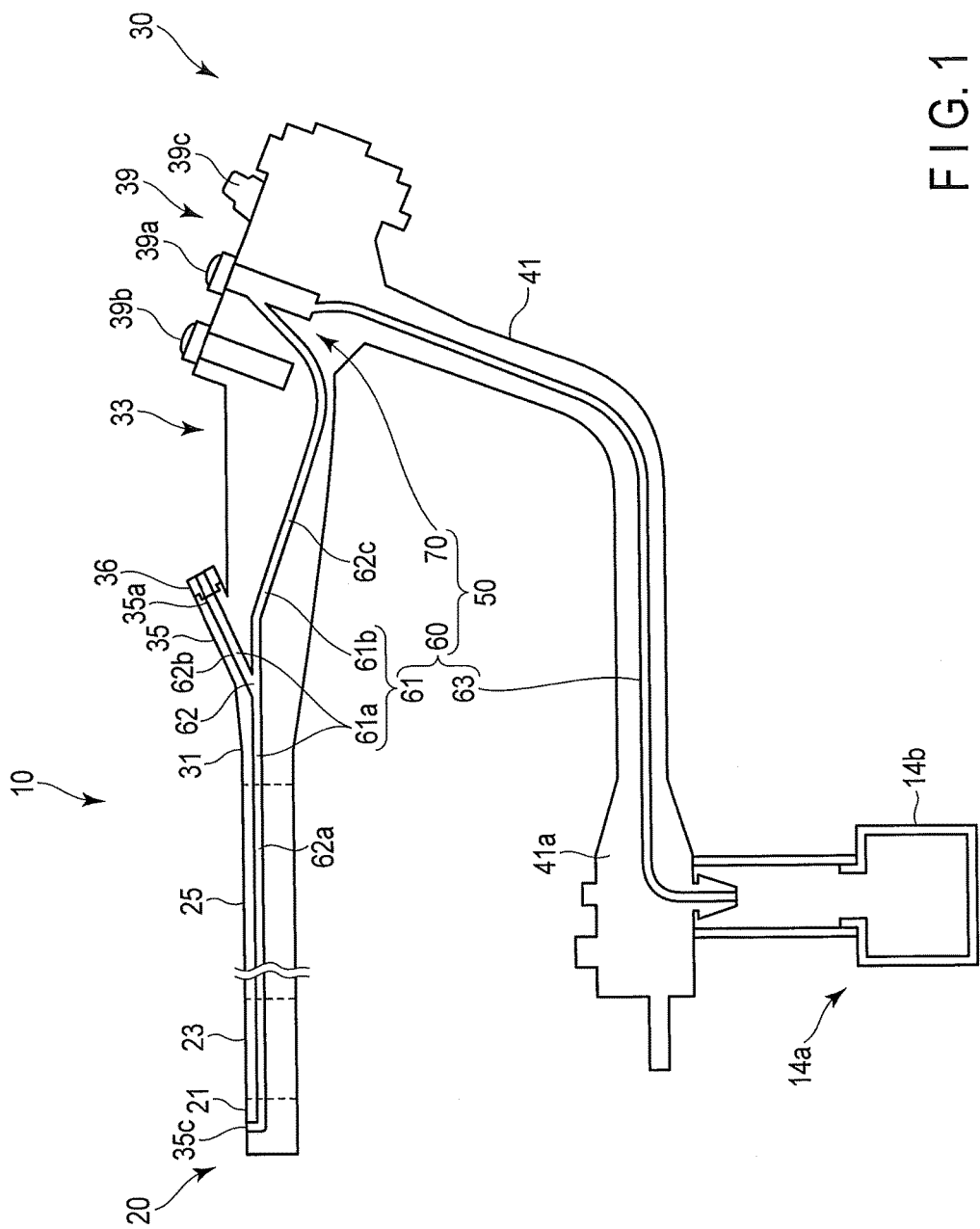
FIG. 1 is a schematic view of a suction mechanism in an endoscope according to a first embodiment of the present invention.

An endoscope 10 as illustrated in FIG. 1 is, for example, a side-viewing endoscope, and functions as an insertion device.

As illustrated in FIG. 1, the endoscope 10 includes a hollow, elongated insertion section 20 which is inserted in a lumen such as a body cavity of a patient, and an operation section 30 which is coupled to a proximal end portion of the insertion section 20 and operates the endoscope 10.

[Insertion Section 20]

As illustrated in FIG. 1, the insertion section 20 includes a distal rigid portion 21, a bendable portion 23 and a flexible tube portion 25, successively in the order from a distal end portion side of the insertion section 20 toward the proximal end portion side of the insertion section 20. A proximal end portion of the distal rigid portion 21 is coupled to a distal end portion of the bendable portion 23, and a proximal end portion of the bendable portion 23 is coupled to a distal end portion of the flexible tube portion 25.

The bendable portion 23 bends in a desired direction, such as an upward, downward, right or left direction, by an operation of a bending operation unit (not shown). By the bending of the bendable portion 23, a position and direction of the distal rigid portion 21 vary. In addition, illumination light is radiated on an observation target, and the observation target is captured within an observation view field. The observation target is, for example, an affected part and a diseased part in a subject (e.g. body cavity).

The flexible tube portion 25 has desired flexibility. Thus, the flexible tube portion 25 is bent by external force. The flexible tube portion 25 is a tubular member extending from a body portion 31 (to be described later) of the operation section 30.

[Operation Section 30]

As illustrated in FIG. 1, the operation section 30 includes the body portion 31 from which the flexible tube portion 25 extends; a grasping portion 33 which is coupled to a proximal end portion of the body portion 31 and is grasped by an operator who operates the endoscope 10; and a universal cord 41 which is connected to the grasping portion 33.

[Grasping Portion 33]

As illustrated in FIG. 1, the grasping portion 33 includes a treatment instrument insertion portion 35, a bending operation section (not shown) which bend-operates the bendable portion 23, and a switch section 39. The treatment instrument insertion portion 35 is disposed on a distal end portion side of the grasping portion 33. The bending operation section and the switch section 39 are disposed on a proximal end portion side of the grasping portion 33.

[Treatment Instrument Insertion Portion 35]

As illustrated in FIG. 1, the treatment instrument insertion portion 35 is branched from the grasping portion 33. Thus, a center axis direction of the treatment instrument insertion portion 35 is inclined to a center axis direction of the grasping portion 33.

As illustrated in FIG. 1, the treatment instrument insertion portion 35 includes a treatment instrument insertion hole portion 35a which is disposed at an end portion of the treatment instrument insertion portion 35 and is provided for inserting a guide member 300 (see FIG. 3B and FIG. 3C) and a treatment instrument 400 (see FIG. 3C), which will be described later, into the endoscope 10.

The treatment instrument insertion hole portion 35a is coupled to a proximal end portion of a treatment instrument insertion channel which functions also as an insertion section-side conduit portion 61a of a first suction conduit portion 61 to be described later. The treatment instrument insertion channel is disposed in the inside of the insertion section 20, and is provided from the flexible tube portion 25 to the distal rigid portion 21 via the bendable portion 23. A distal end portion of the treatment instrument insertion channel communicates with a distal opening portion 35c which is provided in an outer peripheral surface of the distal rigid portion 21. The treatment instrument insertion hole portion 35a is an insertion hole portion for inserting the guide member 300 and treatment instrument 400 into the treatment instrument insertion channel.

As illustrated in FIG. 1, a center axis of the treatment instrument insertion hole portion 35a is disposed coaxial with the center axis of the treatment instrument insertion portion 35, and is thus inclined to the center axis of the grasping portion 33. Furthermore, the center axis direction is inclined to the center axis direction of the grasping portion 33.

As illustrated in FIG. 1, the treatment instrument insertion portion 35 further includes a cylindrical forceps plug portion 36 which is detachably provided on the treatment instrument insertion hole portion 35a. A center axis of the forceps plug portion 36 is disposed coaxial with the center axis of the treatment instrument insertion hole portion 35a. Thus, the forceps plug portion 36 is inclined to the grasping portion 33. When the forceps plug portion 36 is disposed on the treatment instrument insertion hole portion 35a, the forceps plug portion 36 communicates with the treatment instrument insertion channel via the treatment instrument insertion hole portion 35a.

The forceps plug portion 36 has such flexibility as to become openable/closable. This forceps plug portion 36 is formed of, for example, a resin such as rubber.

The forceps plug portion 36 is disposed on the treatment instrument insertion hole portion 35a, and when the treatment instrument 400 is not inserted into the treatment instrument insertion channel via the forceps plug portion 36, the forceps plug portion 36 is closed and the treatment instrument insertion hole portion 35a is closed by the forceps plug portion 36. When the treatment instrument 400 is inserted into the treatment instrument insertion channel via the forceps plug portion 36, the forceps plug portion 36 is closed and the forceps plug portion 36 comes in close contact with the treatment instrument 400.

Figure 3A:
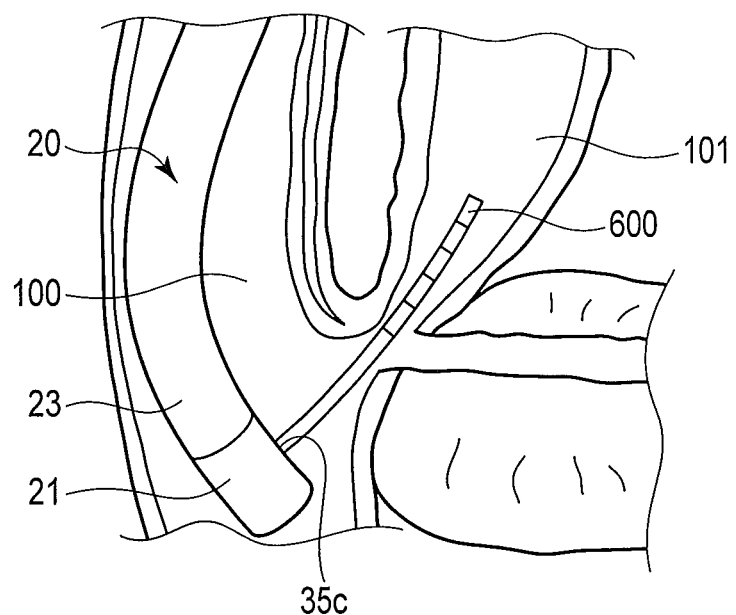
FIG. 3A is a view for describing a contrast tube being inserted into a bile duct.
Figure 3B:
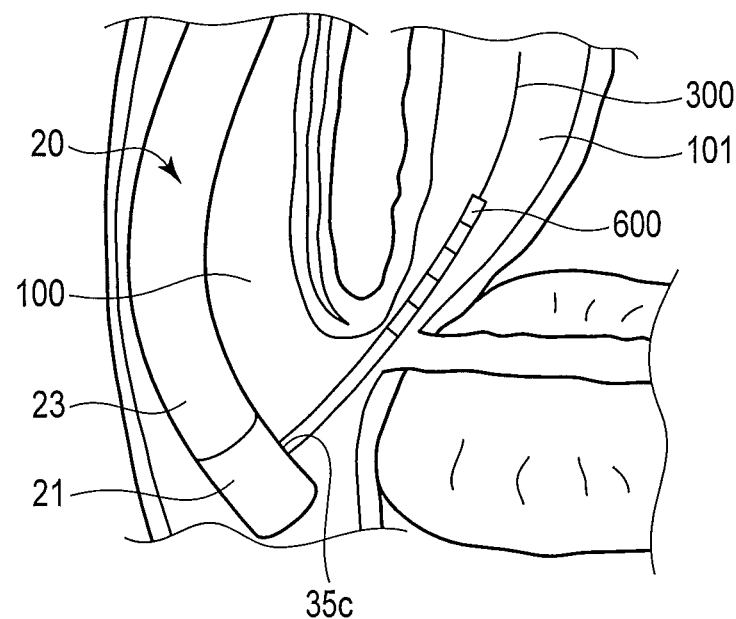
FIG. 3B is a view for describing a guide member being inserted into the bile duct.
Figure 3C:
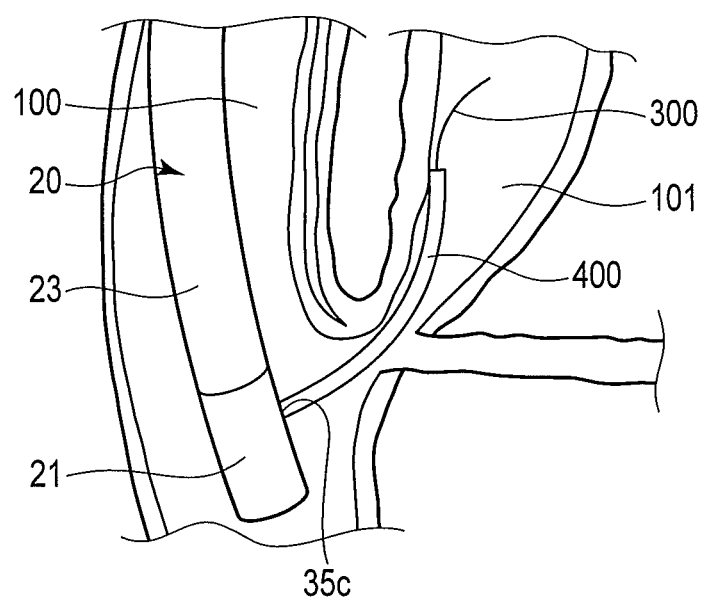
FIG. 3C is a view for describing a treatment instrument being inserted in the bile duct by being guided by the guide member.

The guide member 300 illustrated in FIG. 3B and FIG. 3C and the treatment instrument 400 illustrated in FIG. 3C are inserted into the treatment instrument insertion channel from the forceps plug portion 36 and are pushed in up to the distal rigid portion 21 side. In addition, as illustrated in FIG. 3B and FIG. 3C, the guide member 300 and treatment instrument 400 are projected from the distal opening portion 35c.

[Switch Section 39]

As illustrated in FIG. 1, the switch section 39 includes a suction switch 39a, an air/water feed switch 39b, and various switches 39c for endoscopic imaging. The suction switch 39a, air/water feed switch 39b and various switches 39c are operated by the operator's hand when the grasping portion 33 is held by the operator.

The suction switch 39a is operated when the endoscope 10 sucks fluids, such as a body fluid including mucus and contaminated fluid in a lumen, from the distal opening portion 35c, which serves also as a suction opening portion, via a suction conduit portion 60 to be described later, or in other words, the suction switch 39a is operated in a suction state to be described later.

The air/water feed switch 39b is a part of an air/water feed mechanism (not shown). Since the structure of the air/water feed mechanism is publicly known, a detailed description thereof is omitted here.

[Universal Cord 41]

As illustrated in FIG. 1, the universal cord 41 extends from a side surface of the grasping portion 33. The universal cord 41 includes a connection portion 41a which is connected to a suction device 14a. The suction device 14a includes, for example, a suction pump (not shown), and a suction bottle 14b.

[Suction Mechanism 50 of Endoscope 10]

As illustrated in FIG. 1, the endoscope 10 includes a suction mechanism 50 which is connected to the suction device 14a when the connection portion 41a is connected to the suction device 14a, and which sucks fluids by suction force of the suction pump of the suction device 14a. The fluids include liquids as such as a body fluid including mucus and contaminated fluid in a lumen. A solid, such as a living body tissue, which was sucked by the suction mechanism 50, is included in the sucked fluid which moves in the suction mechanism 50. Such a fluid is stored in the suction bottle 14b.

As illustrated in FIG. 1, the suction mechanism 50 includes a suction conduit portion 60, which includes the distal opening portion 35c serving also as the suction opening portion, and the treatment instrument insertion hole portion 35a; and a fluid plug unit 70 which is connected to the suction conduit portion 60 so as to communicate with the suction conduit portion 60, and which functions as a suction valve unit that is used for suction.

[Suction Conduit Portion 60]

As illustrated in FIG. 1, the suction conduit portion 60 includes a first suction conduit portion 61 including the treatment instrument insertion hole portion 35a, on which the forceps plug portion 36 is provided, and the distal opening portion 35c; and a second suction conduit portion 63 which is connected to the suction device 14a. The distal opening portion 35c sucks the fluid, and the guide member 300 and treatment instrument 400 project from the distal opening portion 35c.

Each of the first suction conduit portion (first conduit) 61 and second suction conduit portion (second conduit) 63, as illustrated in FIG. 1, has a cylindrical shape, for example, a circular cylindrical shape. The first suction conduit portion 61 and second suction conduit portion 63 are formed of, for example, flexible tubes of a resin material or the like.

[First Suction Conduit Portion 61]

As illustrated in FIG. 1, the first suction conduit portion 61 includes a distal end and a proximal end, and passes a fluid between the distal end and the proximal end. Specifically, the first suction conduit portion 61 includes a distal end portion which is provided at the distal end portion of the insertion section 20, and two-forked proximal end portions which are provided on the proximal end side of the insertion section 20. This first suction conduit portion 61 includes the insertion section-side conduit portion 61a which is provided in the inside of the insertion section 20 and body portion 31; and an operation section-side conduit portion 61b which is provided in the inside of the body portion 31 and grasping portion 33.

The insertion section-side conduit portion 61a functions as the treatment instrument insertion channel which is provided from the distal opening portion 35c (suction opening portion) to the treatment instrument insertion hole portion 35a. The treatment instrument insertion hole portion 35a functions as one of the proximal end portions of the first suction conduit portion 61. The insertion section-side conduit portion 61a communicates with the distal opening portion 35c and treatment instrument insertion hole portion 35a.

The operation section-side conduit portion 61b is provided from a two-forked portion 62 of the first suction conduit portion 61, which is coupled to the insertion section-side conduit portion 61a, to the fluid plug unit 70. The fluid plug unit 70 functions as the other proximal end portion of the first suction conduit portion 61. The operation section-side conduit portion 61b communicates with the insertion section-side conduit portion 61a at the two-forked portion 62, and communicates with the fluid plug unit 70 at a proximal end portion of the operation section-side conduit portion 61b.

In this manner, the first suction conduit portion 61 is connected to, and communicates with, the distal opening portion 35c, the treatment instrument insertion hole portion 35a on which the forceps plug portion 36 is provided, and the fluid plug unit 70.

If the above-described content is restated, the first suction conduit portion 61 includes a distal conduit portion 62a which is coupled to the distal opening portion 35c, a first proximal conduit portion 62b which is coupled to the treatment instrument insertion hole portion 35a, and a second proximal conduit portion 62c which is coupled to the fluid plug unit 70. The distal conduit portion 62a, first proximal conduit portion 62b and second proximal conduit portion 62c communicate with, and are connected to, each other at the two-forked portion 62. The distal conduit portion 62a and first proximal conduit portion 62b function as the insertion section-side conduit portion 61a, and the second proximal conduit portion 62c function as the operation section-side conduit portion 61b.

The first suction conduit portion 61 includes the forceps plug portion 36 into which the treatment instrument 400 is inserted, and the distal opening portion 35c from which the treatment instrument 400 projects and which sucks a fluid.

[Second Suction Conduit Portion 63]

As illustrated in FIG. 1, the second suction conduit portion 63 is provided from the fluid plug unit 70 to the connection portion 41a via the universal cord 41. A distal end portion of the second suction conduit portion 63 communicates with the fluid plug unit 70. A proximal end portion of the second suction conduit portion 63 communicates with the suction device 14a when the connection portion 41a is connected to the suction device 14a.

In this manner, the second suction conduit portion 63 is provided in the inside of the grasping portion 33 and universal cord 41. In addition, the second suction conduit portion 63 is connected to the suction device 14a, and passes a fluid.

[Suction Conduit Portion 60 in Suction Mechanism 50]

In the suction mechanism 50, when the connection portion 41a is connected to the suction device 14a, the first suction conduit portion 61 sucks, by the suction force of the suction device 14a, a fluid by passing the fluid from the distal opening portion 35c, which is the distal end portion of the first suction conduit portion 61, to the fluid plug unit 70 via the two-forked portion 62, the fluid plug unit 70 being provided at the proximal end portion of the first suction conduit portion 61. Thus, the fluid flows from the distal conduit portion 62a through the second proximal conduit portion 62c via the two-forked portion 62, and is sucked into the fluid plug unit 70.

The second suction conduit portion 63 sucks, by the suction force of the suction device 14a, the fluid by passing the fluid from the fluid plug unit 70, which is provided at the distal end portion of the second suction conduit portion 63, to the suction device 14*a* which is provided at the proximal end portion of the second suction conduit portion 63. Thus, the fluid flows from the fluid plug unit 70 through the second suction conduit portion 63, and is sucked into the suction device 14*a*.

[Fluid Plug Unit 70]

As is illustrated in FIG. 1, FIG. 2A and FIG. 2B, the fluid plug unit 70 is provided in the grasping portion 33. As described above, the fluid plug unit 70 is connected to the first suction conduit portion 61 and second suction conduit portion 63, and communicates with the first suction conduit portion 61 and second suction conduit portion 63.

As illustrated in FIG. 2A and FIG. 2B, the fluid plug unit 70 includes a cylinder 71 which is connected to the first suction conduit portion 61 and second suction conduit portion 63 such that the first suction conduit portion 61 and second suction conduit portion 63 communicate each other; and the suction switch 39*a* including a pushing portion 391*b* and a piston 73.

As illustrated in FIG. 1, FIG. 2A and FIG. 2B, the pushing portion 391*b* is an operation portion which is operated in order to switch one of a leakage suppression state (a first position, a release position, an auto-suction state; see FIG. 2A) and the suction state (a second position, a pushed position, a pushed state; see FIG. 2B) to the other, for example, when the insertion section 20 is inserted in a lumen. This switching is implemented by the movement of the piston 73 relative to the cylinder 71. A pressure on the distal opening portion 35*c* side refers to, for example, the pressure in the lumen into which the distal end side of the insertion section 20 is inserted. In the leakage suppression state, outside air is caused to flow into the cylinder 71 by the suction device 14*a*, and the fluid is sucked in the second suction conduit portion 63. Thus, in the leakage suppression state, the fluid is suppressed from being sucked from the distal opening portion 35*c* and leaking to the outside from the forceps plug portion 36 through the first suction conduit portion 61, as the pressure on the distal opening portion 35*c* side becomes higher than the outside air pressure on the forceps plug portion 36 side. In other words, in the leakage suppression state, a fluid which has a higher pressure than the outside air pressure on the distal opening portion 35*c* side, is suppressed from leaking to the outside from the forceps plug portion 36 through the first suction conduit portion 61. The suction state is a state in which, regardless of whether the pressure on the distal opening portion 35*c* side is higher than the outside air pressure on the forceps plug portion 36 side, the fluid is sucked from the distal opening portion 35*c* by the suction device 14*a*, and the fluid is forcibly sucked by the suction device 14*a* via the first suction conduit portion 61 and second suction conduit portion 63.

In the leakage suppression state illustrated in FIG. 2A, in order to suppress the fluid from being discharged from the forceps plug portion 36 by a pressure difference when the pressure at the distal opening portion 35*c* is higher than the outside air pressure on the forceps plug portion 36 side, the fluid is sucked into the suction bottle 14*b* from the first suction conduit portion 61 through the fluid plug unit 70 and second suction conduit portion 63. In the leakage suppression state, when there is no pressure difference between the pressure at the distal opening portion 35*c* and the outside air pressure on the forceps plug portion 36 side, outside air continues to be sucked from a vent hole portion 73*a* of the piston 73 into the suction device 14*a* via an internal space of the piston 73, an internal space of the cylinder 71 and the second suction conduit portion 63. Although details will be described later, the suction in the leakage suppression state is implemented by the suction of the suction device 14*a* in substantially the same manner as in the suction state.

In the suction state illustrated in FIG. 2B, the fluid is sucked from the distal opening portion 35*c* by the suction device 14*a*, flows through the first suction conduit portion 61, fluid plug unit 70 and second suction conduit portion 63, and is stored in the suction bottle 14*b*.

As illustrated in FIG. 2A and FIG. 2B, the cylinder 71 communicates with the first suction conduit portion 61 and second suction conduit portion 63, such that the first suction conduit portion 61 and second suction conduit portion 63 communicate with each other. The piston 73 is detachably fittingly inserted in this cylinder 71, and is movable in the axial direction of the cylinder 71 relative to the cylinder 71 in accordance with an operation of the pushing portion 391*b*. In addition, as illustrated in FIG. 2A and FIG. 2B, the fluid plug unit 70 switches one of the leakage suppression state illustrated in FIG. 2A and the suction state illustrated in FIG. 2B to the other, by moving the piston 73 relative to the cylinder 71 in accordance with a pushing operation or a releasing operation (non-operation) of the pushing portion 391*b*.

Specifically, if the operation (pushed) state of the pushing portion 391*b* illustrated in FIG. 2A is switched to the non-operation (released) state, the piston 73 moves upward by an urging member 77 (to be described later), and the fluid plug unit 70 is switched from the suction state to the leakage suppression state. As illustrated in FIG. 2B, if the pushing portion 391*b* is push-operated and the piston 73 is pushed inside the grasping portion 33 in a axial direction of the piston 73, the fluid plug unit 70 is switched from the leakage suppression state to the suction state.

In other words, by the piston 73 moving in a axial direction of the cylinder 71 relative to the cylinder 71, the fluid plug unit 70 switches one of the leakage suppression state illustrated in FIG. 2A and the suction state illustrated in FIG. 2B to the other. Specifically, by the piston 73 being fittingly inserted into the cylinder 71 and moving in the axial direction of the cylinder 71, the piston 73 switches one of a first position where the fluid in the first suction conduit portion 61 that is the first conduit is suppressed from leaking to the outside from the forceps plug portion 36, and a second position where the fluid is sucked by the suction device 14*a* via the first conduit and the second suction conduit portion 63 that is the second conduit, to the other.

The cylinder 71 has, for example, a cylindrical shape having a center axis C. The cylinder 71 is formed of, for example, a metallic material such as stainless steel.

As illustrated in FIG. 2A and FIG. 2B, the cylinder 71 includes one end portion 71*a* which opens such that the piston 73 is fittingly inserted into the cylinder 71, and the other end portion 71*b* which opens, and to which the second suction conduit portion 63 is connected such that the second suction conduit portion 63 communicates with the cylinder 71. The one end portion 71*a* functions as an insertion hole portion through which the piston 73 is fittingly inserted into the cylinder 71. As illustrated in FIG. 2A and FIG. 2B, the cylinder 71 further includes a side-surface opening portion 71*c* to which the first suction conduit portion 61 is connected such that the first suction conduit portion 61 communicates with the cylinder 71.

As illustrated in FIG. 2A and FIG. 2B, the cylinder 71 is insertable/drawable into/from a hole portion 33*a* which is provided in the grasping portion 33, the one end portion 71*a* of the cylinder 71 is fixed to the grasping portion 33, and the other end portion 71b of the cylinder 71 is disposed within the grasping portion 33. An O-ring (not shown) or the like is provided at the one end portion 71a of this cylinder 71. Thereby, between the cylinder 71 and the grasping portion 33, infiltration of a liquid into the inside of the endoscope 10 from the outside is prevented. In short, liquid-tightness and air-tightness in the inside of the operation section 30 can be secured.

The piston 73 has a cylindrical shape which is elongated in the axial direction of the piston 73.

In the meantime, since the piston 73 is washed with a chemical or the like, the piston 73 is formed of a material with chemical resistance. This piston 73 is formed of, for example, at least one of polypropylene, polycarbonate, nylon, a sulfone-based resin such as polysulfone or polyphenylsulfone, a liquid crystal polymer, denatured polyphenylene ether, and polyether ether ketone.

As illustrated in FIG. 2A and FIG. 2B, the piston 73 includes one end portion which is disposed on the outside of the cylinder 71 (grasping portion 33) and is, for example, screw-engaged with the plate-shaped pushing portion 391b, and the other end portion (opening end portion) disposed in the inside of the cylinder 71. In the present embodiment, the outside diameter of the piston 73 is substantially equal to the inside diameter of the cylinder 71 such that the piston 73 secures a liquid-tight state with the cylinder 71. Thus, the outer peripheral surface of the piston 73 slides on the inner peripheral surface of the cylinder 71. In the meantime, as illustrated in FIG. 2A, the piston 73 includes the vent hole portion 73a which is provided on the one end portion side, and takes outside air into the inside of the piston 73.

As illustrated in FIG. 2A and FIG. 2B, the piston 73 is attached to an attachment portion 75 disposed on the one end portion side of the piston 73. The attachment portion 75 is disposed such that the piston 73 is inserted through the attachment portion 75 and the attachment portion 75 surrounds the one end portion side of the piston 73. The attachment portion 75 has a cylindrical shape with a bottom surface 75a on one side. The bottom surface 75a has an insertion hole 75b for insertion of the piston 73. The bottom surface 75a abuts on a flange portion 33c which is provided at a periphery of the hole portion 33a. In the axial direction of the piston 73, the bottom surface 75a is provided under the pushing portion 391b. The attachment portion 75 is formed of, for example, a soft material such as rubber.

As illustrated in FIG. 2A and FIG. 2B, the urging member 77 of the suction switch 39a is disposed between the bottom surface 75a and pushing portion 391b, and abuts on the bottom surface 75a and pushing portion 391b, in the axial direction of the piston 73. The urging member 77 is disposed such that the urging member 77 is wound around the piston 73 that is exposed from the cylinder 71. As the urging member 77, for example, a metallic coil spring is used. The urging member 77 is expandable/contractible in the axial direction of the piston 73. The urging member 77 has such urging force as to urge the pushing portion 391b upward in FIG. 2A (toward the outside of the grasping portion 33) along the center axis C, and to urge the piston 73 upward (toward the outside of the grasping portion 33). At this time, the flange portion 33c and bottom surface 75a abut on each other, and push each other. Thereby, the bottom surface 75a prevents the piston 73 from being drawn out of the attachment portion 75. The urging member 77 is surrounded by the attachment portion 75.

In the meantime, it is preferable that the pushing portion 391b, piston 73, attachment portion 75 and urging member 77 are integrally formed as one body. By the integral formation, the suction switch 39a can be attached/detached, as one unit, to/from the flange portion 33c by the attachment portion 75. It is preferable that the piston 73 according to this embodiment is positioned in a circumferential direction. For example, the piston 73 is positioned in the circumferential direction, by the attachment portion 75 and flange portion 33c being properly formed.

As illustrated in FIG. 2A, if the pushing portion 391b is switched from the operation (pushed) state to the non-operation (released) state, the urging member 77 expands, and the urging member 77 urges the piston 73 upward via the pushing portion 391b. Thus, the piston 73 moves upward, and the fluid plug unit 70 switches from the suction state to the leakage suppression state.

As illustrated in FIG. 2B, if the pushing portion 391b is operated (pushed), the urging member 77 contracts. Thus, the piston 73 moves downward, and the fluid plug unit 70 switches from the leakage suppression state to the suction state.

The suction mechanism 50 includes a leakage suppression passage portion 80 which is a first passage, and a suction passage portion 90 which is a second passage.

As illustrated in FIG. 2A and FIG. 2B, the leakage suppression passage portion 80 includes a leakage suppression through-hole 81 which is provided such that the leakage suppression through-hole 81 penetrates a peripheral surface of the piston 73, and communicates with the first suction conduit portion 61 in the leakage suppression state. The leakage suppression passage portion 80 further includes an internal space of the piston 73 (hereinafter referred to as "piston internal space portion 731") which communicates with the leakage suppression through-hole 81, and an internal space of the cylinder 71 (hereinafter referred to as "cylinder internal space portion 711") which communicates with the piston internal space portion 731. It is preferable that the leakage suppression through-hole 81 has, for example, a circular shape.

In accordance with the movement of the piston 73, the leakage suppression passage portion 80 establishes communication between the first suction conduit portion 61 and second suction conduit portion 63 in the leakage suppression state illustrated in FIG. 2A, and permits suction. Thus, in the leakage suppression state illustrated in FIG. 2A, a fluid is passed through the leakage suppression passage portion 80.

Specifically, the leakage suppression passage portion 80, which is the first passage, communicates with the first suction conduit portion 61 which is the first conduit, and the second suction conduit portion 63 which is the second conduit, when the piston 73 is disposed in the first position that is the leakage suppression state illustrated in FIG. 2A.

In accordance with the movement of the piston 73, the leakage suppression passage portion 80 does not communicate with the first suction conduit portion 61 in the suction state illustrated in FIG. 2B, that is, the leakage suppression passage portion 80 is shut off from the first suction conduit portion 61, but the leakage suppression passage portion 80 keeps the state of communication with the second suction conduit portion 63. Thus, in the suction state illustrated in FIG. 2B, the leakage suppression passage portion 80 is set in the state in which the leakage suppression passage portion 80 does not suck.

Specifically, when the piston 73 is disposed in the second position that is the suction state illustrated in FIG. 2B, the leakage suppression passage portion 80 that is the first passage shuts off communication with the first suction conduit portion 61 that is the first conduit.

The suction passage portion 90 includes a suction through-hole 91 which is provided such that the suction through-hole 91 penetrates the peripheral surface of the piston 73, and communicates with the first suction conduit portion 61 in the suction state. The suction passage portion 90 further includes the above-described piston internal space portion 731 which also communicates with the suction through-hole 91, and the above-described cylinder internal space portion 711. It is preferable that the suction through-hole 91 has, for example, a circular shape.

In accordance with the movement of the piston 73, the suction passage portion 90 does not communicate with the first suction conduit portion 61 in the leakage suppression state illustrated in FIG. 2A, that is, the suction passage portion 90 is shut off from the first suction conduit portion 61, but the suction passage portion 90 communicates with the second suction conduit portion 63. Thus, in the leakage suppression state illustrated in FIG. 2A, the suction passage portion 90 is set in the state in which the suction passage portion 90 does not suck.

In accordance with the movement of the piston 73, the suction passage portion 90 communicates with the first suction conduit portion 61 and second suction conduit portion 63 in order to permit suction in the suction state illustrated in FIG. 2B, and permits suction of a fluid. Thus, in the suction state illustrated in FIG. 2B, the fluid is passed through the suction passage portion 90.

Specifically, in accordance with the movement of the piston 73, the suction passage portion 90 which is the second passage, shuts off communication with the first suction conduit portion 61 which is the first conduit, when the piston 73 is disposed in the first position that is the leakage suppression state illustrated in FIG. 2A, and the suction passage portion 90 communicates with the first suction conduit portion 61 which is the first conduit, and the second suction conduit portion 63 which is the second conduit, and permits suction of the fluid, when the piston 73 is disposed in the second position that is the suction state illustrated in FIG. 2B.

In this manner, by the movement of the piston 73 relative to the cylinder 71 as illustrated in FIG. 2A and FIG. 2B, either the leakage suppression passage portion 80 or the suction passage portion 90 communicates with the first suction conduit portion 61.

The leakage suppression through-hole 81 and suction through-hole 91 are disposed coaxial with each other. In addition, the leakage suppression through-hole 81 is disposed at a greater distance from the pushing portion 391b than the suction through-hole 91 in the axial direction of the piston 73.

The piston internal space portion 731 and cylinder internal space portion 711 serve also as the leakage suppression passage portion 80 and suction passage portion 90, are shared by the leakage suppression passage portion 80 and suction passage portion 90, and are used in each of the leakage suppression state and suction state. In addition, as illustrated in FIG. 2A and FIG. 2B, the leakage suppression passage portion 80 and suction passage portion 90 always communicate with the second suction conduit portion 63, regardless of the movement of the piston 73, or in other words, in each of the leakage suppression state and suction state.

As illustrated in FIG. 2A, if the pushing portion 391b is non-operated (is released), that is, in the state in which the pushing portion 391b is not pushed, the piston 73 keeps the state in which the piston 73 is moved upward by the urging force of the urging member 77. At this time, the fluid plug unit 70 enters the leakage suppression state, the leakage suppression passage portion 80 communicates with the first suction conduit portion 61, and the suction passage portion 90 does not communicate with the first suction conduit portion 61.

In this case, the leakage suppression passage portion 80 establishes communication between the first suction conduit portion 61 and second suction conduit portions 63 in order to perform suction in the leakage suppression state. In other words, in the leakage suppression state, the leakage suppression passage portion 80 establishes communication between the distal opening portion 35c side and the suction device 14a side.

As illustrated in FIG. 2B, if the pushing portion 391b is pushed down, the piston 73 is moved downward by the pushing portion 391b. Thereby, the fluid plug unit 70 is switched from the leakage suppression state to the suction state, the leakage suppression passage portion 80 does not communicate with the first suction conduit portion 61, that is, the leakage suppression passage portion 80 is shut off from the first suction conduit portion 61, and the suction passage portion 90 communicates with the first suction conduit portion 61.

In this case, the suction passage portion 90 establishes communication between the first suction conduit portion 61 and second suction conduit portions 63 in order to perform suction in the suction state. In other words, in the suction state, the suction passage portion 90 establishes communication between the distal opening portion 35c side and the suction device 14a side.

In the present embodiment, the leakage suppression passage portion 80 that is the first passage at a time when the piston 73 is disposed in the first position that is the leakage suppression state illustrated in FIG. 2A, has such a structure that the fluid flows less easily in the state in which the fluid is sucked by the suction device 14a, compared to the suction passage portion 90 that is the second passage at a time when the piston 73 is disposed in the second position that is the suction state illustrated in FIG. 2B. Specifically, an amount of opening of the leakage suppression passage portion 80 is smaller than an amount of opening of the suction passage portion 90. Concretely, as illustrated in FIG. 2A and FIG. 2B, for example, a diameter of the leakage suppression through-hole 81 is less than a diameter of the suction through-hole 91. Alternatively, the amount of opening of the leakage suppression passage portion 80 is smaller than an amount of opening of a communication portion 61c of the first suction conduit portion 61 which communicates with the leakage suppression passage portion 80. It is preferable that the communication portion 61c of the first suction conduit portion 61 in relation to the cylinder 71 has, for example, a circular shape. Concretely, a diameter of the leakage suppression through-hole 81 is less than a diameter of the communication portion 61c of the first suction conduit portion 61 which communicates with the leakage suppression passage portion 80. Thus, as regards the leakage suppression passage portion 80 and suction passage portion 90, the resistance of the leakage suppression passage portion 80, which indicates the difficulty of flow of the fluid in the leakage suppression passage portion 80, is greater than the resistance of the suction passage portion 90, which indicates the difficulty of flow of the fluid in the suction passage portion 90. In addition, the fluid in the leakage suppression passage portion 80 in the leakage suppression state in the state in which the fluid is sucked by the suction device 14a flows less easily than the fluid in the suction passage portion 90 in the suction state in the state in which the fluid is sucked by the suction device 14a.

In the meantime, if the suction property in the suction state, or in other words, clogging in the suction state, is considered, it is preferable that the diameter of the suction through-hole 91 is identical to the diameter of the communication portion 61c, or is greater than the diameter of the communication portion 61c.

As described above, the suction device 14a is always driven in the leakage suppression state and in the suction state, and suction is performed, for example, in each of the leakage suppression state and the suction state. In this suction, in the leakage suppression state, suction is performed in order to suppress the fluid from leaking to the outside from the forceps plug portion 36. On the other hand, in the suction state, suction is performed in order to cause the fluid to be sucked into the suction device 14a. Specifically, in the suction state, the fluid is sucked by the suction force of the suction device 14a from the distal opening portion 35c into the first suction conduit portion 61. The sucked fluid flows, by the suction force, from the first suction conduit portion 61 to the suction device 14a via the fluid plug unit 70 and second suction conduit portion 63, and is sucked into the suction device 14a.

[Operation]

When the endoscope 10 is used, the suction device 14a is always driven, and continues to exhibit a suction function. As illustrated in FIG. 2A, when the pushing portion 391b is non-operated (is released), the leakage suppression through-hole 81 with the diameter, which is less than the diameter of the suction through-hole 91, communicates with the first suction conduit portion 61. Thereby, the leakage suppression state is kept in the fluid plug unit 70.

In the leakage suppression state, when there is no difference between the pressure on the distal opening portion 35c side of the insertion section 20 and the outside air pressure on the forceps plug portion 36 side, outside air continues to be sucked from the vent hole portion 73a into the suction device 14a via the piston internal space portion 731, cylinder internal space portion 711 and second suction conduit portion 63.

The insertion section 20 is inserted in a lumen as desired. It is assumed that in the leakage suppression state, the pressure on the distal opening portion 35c side in the lumen has become gradually higher than the outside air pressure on the forceps plug portion 36 side on the outside of the lumen. Then, the pressure in the distal conduit portion 62a becomes gradually higher than the pressure in the first proximal conduit portion 62b. In addition, the pressure in the distal conduit portion 62a becomes gradually higher than the pressure in the second proximal conduit portion 62c. In the leakage suppression state, the suction force of the suction device 14a always acts in the cylinder internal space portion 711. Thus, in the second proximal conduit portion 62c which communicates with the cylinder internal space portion 711 via the leakage suppression through-hole 81, and in the first proximal conduit portion 62b provided at a greater distance from the cylinder internal space portion 711 than the second proximal conduit portion 62c, the pressure in the second proximal conduit portion 62c becomes gradually lower than the pressure in the first proximal conduit portion 62b by an action of the suction force.

Thereby, the fluid flows more easily from the distal conduit portion 62a to the second proximal conduit portion 62c via the two-forked portion 62, than from the distal conduit portion 62a to the first proximal conduit portion 62b via the two-forked portion 62, and flows the fluid plug unit 70. Furthermore, in the fluid plug unit 70, the fluid flows into the second suction conduit portion 63 which communicates with the cylinder 71, via the leakage suppression through-hole 81 communicating with the second proximal conduit portion 62c, the piston internal space portion 731 and the cylinder internal space portion 711. Then, the fluid continues to be sucked into the suction bottle 14a through the second suction conduit portion 63 by the suction of the suction device 14a.

Thereby, the fluid is prevented from being discharged from the forceps plug portion 36 through the first proximal conduit portion 62b by the pressure difference.

In the meantime, in the case where there is no difference between the pressure on the distal opening portion 35c side of the insertion section 20 and the outside air pressure on the forceps plug portion 36 side, since the distal opening portion 35c is located at a greater distance from the cylinder internal space portion 711 than the vent hole portion 73a, most of the suction acts on the vent hole portion 73a. Thus, in the leakage suppression state, and in the case in which there is no difference between the pressure on the distal opening portion 35c side of the insertion section 20 and the outside air pressure on the forceps plug portion 36 side, the suction from the distal opening portion 35c side is moderated.

As illustrated in FIG. 2B, if the pushing portion 391b is operated (pushed), the piston 73 moves downward relative to the cylinder 71, the communication between the first suction conduit portion 61 and the leakage suppression through-hole 81 is shut off, and the suction through-hole 91 with the diameter which is greater than the diameter of the leakage suppression through-hole 81, communicates with the first suction conduit portion 61. Thus, the fluid plug unit 70 is switched to the suction state. By the suction, the fluid flows from the distal conduit portion 62a via the two-forked portion 62 to the fluid plug unit 70 through the second proximal conduit portion 62c. In the fluid plug unit 70, the fluid flows into the second suction conduit portion 63 which communicates with the cylinder 71, via the suction through-hole 91 communicating with the second proximal conduit portion 62c, the piston internal space portion 731 and the cylinder internal space portion 711. Then, the fluid continues to be sucked in the suction bottle 14b through the second suction conduit portion 63.

The resistance of the leakage suppression passage portion 80, which indicates the difficulty of flow of the fluid in the leakage suppression passage portion 80, is greater than the resistance of the suction passage portion 90, which indicates the difficulty of flow of the fluid in the suction passage portion 90. Thereby, at a treatment time and an observation time which are included in the leakage suppression state, it is possible to prevent the fluid from being sucked, when not intended, in the distal opening portion 35c, leading to problems with the treatment and observation.

The leakage suppression passage portion 80 includes the leakage suppression through-hole 81, and the suction passage portion 90 includes the suction through-hole 91. Thereby, the above can be implemented with a simple configuration.

The leakage suppression through-hole 81 is disposed coaxial with the suction through-hole 91. Thereby, by the pushing portion 391b simply pushing or releasing the piston 73, one of the leakage suppression state and the suction state is easily switched to the other.

In the meantime, the side-viewing endoscope 10 is used for, for example, endoscopic retrograde cholangiopancreatography (hereinafter referred to as "ERCP").

ERCP is an operation method in which, as illustrated in FIG. 3A, FIG. 3B and FIG. 3C, a contrast medium is injected in a lumen such as a bile duct 101, and a biliary tract system and a pancreatic duct, which are affected parts in the lumen, are photographed and examined, and the affected parts are treated by the treatment instrument 400. In the ERCP, the treatment instrument 400 is guided to the affected part by the guide member 300

The guide member 300 is formed of, for example, a fine line-shaped member. The line-shaped member includes, for example, a stainless-steel wire. The line-shaped member may include, for example, a nickel-titanium wire having a surface coated with, for example, a fluororesin.

The treatment instrument 400 includes, for example, a knife for endoscopic sphincterotomy (hereinafter referred to as "EST"), a cannula, a guide wire, a scissors-like treatment instrument, a tweezers-like treatment instrument, a forceps, a basket-like treatment instrument for breaking a stone, and a basket-like treatment instrument for taking a stone out of the body without breaking the stone. The treatment instrument 400 is formed of, for example, a fine line-shaped member.

The treatment instrument 400 includes an insertion hole portion (not shown) through which the guide member 300 as illustrated in FIG. 3C can be inserted. The treatment instruction 400 can slide on the guide member 300 so that the guide member 300 may be inserted through the insertion hole portion. By this sliding, the treatment instrument 400 can move along the guide member 300.

An example of the procedure of ERCP is as follows.

As illustrated in FIG. 3A, the insertion section 20 is inserted in a lumen such as the duodenum 100, and a contrast tube 600 called "cannula" is inserted into the bile duct 101 from the forceps plug portion 36 via the treatment instrument insertion channel (insertion section-side conduit portion 61a) and the distal opening portion 35c. Next, a contrast medium is injected in a subject such as the bile duct 101 via the contrast tube 600, and the subject such as the bile duct 101 is photographed by roentgen photography or the like.

As illustrated in FIG. 3B, the guide member 300 is inserted into the contrast tube 600, and a distal end portion of the guide member 300 projects from a distal end of the contrast tube 600. Then, the distal end portion of the guide member 300 reaches the subject such as the bile duct 101. In the meantime, a proximal end portion of the guide member 300 is exposed to the outside of the endoscope 10 from the forceps plug portion 36. Then, in the state in which the guide member 300 is left in the subject such as the bile duct 101, only the contrast tube 600 is pulled out of the endoscope 10.

Next, when the treatment instrument 400 moves along the guide member 300, the treatment instrument 400 is guided by the guide member 300, and is inserted into the treatment instrument insertion channel from the forceps plug portion 36. Then, in the state in which the treatment instrument 400 is guided by the guide member 300, the treatment instrument 400 projects to the lateral side from the distal opening portion 35c, and reaches the subject.

In this manner, the treatment instrument 400 is guided by the guide member 300 up to the subject, and treats the affected part.

In the above-described ERCP, for example, when the insertion section 20 was inserted in the duodenum (lumen) 100, there is a case in which the pressure inside the duodenum 100 in which the insertion section 20 was inserted (the pressure on the distal end side of the insertion section 20) becomes higher than, for example, the outside air pressure at the forceps plug portion 36. For example, there is a case in which, for example, by the air feed operation of the endoscope 10, the pressure in the lumen in which the insertion section 20 was inserted becomes higher than, for example, the outside air pressure at the forceps plug portion 36.

In this case, even in the state illustrated in FIG. 2A in which the pushing portion 391b is released, there is concern that a fluid flows into the first suction conduit portion 61 along the treatment instrument 400.

There is concern that the fluid which has flowed in the first suction conduit portion 61, the fluid remaining in the suction conduit portion 60, and the fluid remaining in the fluid plug unit 70 leak to the outside from, for example, the forceps plug portion 36. The fluid remaining in the suction conduit portion 60 includes, for example, a fluid remaining in the insertion section-side conduit portion 61a that is the treatment instrument insertion channel by the use of the treatment instrument 400, and a fluid which was not sucked by the suction device 14a when the fluid was sucked into the endoscope 10, and remains in the operation section-side conduit portion 61b and the second suction conduit portion 63.

In the present embodiment, the suction device 14a is always driven even in a state during treatment, a treatment instrument replacement state, an observation state and the leakage suppression state including a non-operation (released) state, as illustrated in FIG. 2A, the leakage suppression conduit portion 80 establishes communication between the first suction conduit portion 61 and second suction conduit portion 63 in the leakage suppression state. In other words, the leakage suppression conduit portion 80 establishes communication between the distal opening portion 35c side and the suction device 14a side. Thus, the suction force always acts in the leakage suppression conduit portion 80, first suction conduit portion 61 and second suction conduit portion 63. In other words, the suction force acts up to the distal opening portion 35c side. Thus, the fluid remaining in the first suction conduit portion 61, second suction conduit portion 63 and fluid plug unit 70 is affected by the suction force by the above-described communication, if not in the suction state. As a result, the fluid is exactly sucked, for example, by the suction device 14a.

In this manner, the fluid is suppressed from leaking to the outside from the forceps plug portion 36.

By the above, leakage is suppressed even if use is made of the treatment instrument 40 with which the forceps plug portion 36 is not easily put in close contact. In other words, in order to suppress leakage, it is not necessary to put the forceps plug portion 36 in firm and close contact with the treatment instrument 400. Thus, degradation of insertion-removal properties of the treatment instrument 400 can be prevented.

By the above, fluid leakage is suppressed. Thus, it is not necessary to loosen the close contact between the treatment instrument 400 and forceps plug portion 36 in order to replace the treatment instrument 400 and to move advance/retreat the treatment instrument 400. The leakage of the fluid to the outside from the forceps plug portion 36 due to loosening of close contact can further be suppressed.

In this manner, it is possible to suppress a fluid from leaking from the forceps plug portion 36, depending on the condition of use of the treatment instrument 400 and endoscope 10.

Advantageous Effects

As described above, in the present embodiment, even if the pressure in the lumen such as the duodenum 100 becomes higher than the outside air pressure, it is possible to suppress a fluid from leaking from the forceps plug portion 36. In this embodiment, while the leakage of fluid from the forceps plug portion 36 is suppressed, it is possible to prevent the degradation of insertion-removal properties of the treatment instrument 400 to the forceps plug portion 36.

In the present embodiment, the suction device 14*a* is always driven in the leakage suppression state and in the suction state, the suction force is fixed and equal, for example, between the leakage suppression state and the suction state. In each of the leakage suppression state and the suction state, this suction force acts, for example, on the affected part in the subject and on the fluid such as a body fluid, via the suction mechanism 50 and distal opening portion 35*c*.

The leakage suppression state includes the state during treatment, in which the affected part is being treated by the treatment instrument 400, the replacement state in which the treatment instrument 400 is replaced, the observation state in which the affected part is observed, and the non-operation state (released state) in which the suction switch 39*a* is not operated.

Thus, as described above, if the suction force in the leakage suppression state is equal to the suction force in the suction state, the suction force in the leakage suppression state, like the suction force in the suction state, would act on the affected part via the suction mechanism 50 and distal opening portion 35*c*. In addition, in the leakage suppression state, the affected part would be pulled into the distal opening portion 35*c* as in the suction state by the action force, such as suction force, which acts on the affected part as in the suction state. Thus, in the leakage suppression state including the state during treatment and the observation state, if the affected part is pulled into the distal opening portion 35*c* as in the suction state, there is concern that problems occur with the treatment and observation.

Thus, in the leakage suppression state which is the state other than the suction state, such action force as in the suction state is not needed. In other words, it is necessary to make the action force in the leakage suppression state smaller than the action force in the suction state.

Hence, in this embodiment, the resistance of the leakage suppression passage portion 80 is higher than the resistance of the suction passage portion 90. Specifically, the amount of opening of the leakage suppression passage portion 80 is smaller than the amount of opening of the suction passage portion 90, or the amount of opening of the leakage suppression passage portion 80 is smaller than the amount of opening of the communication portion 61*c* which communicates with the leakage suppression passage portion 80. Thereby, in this embodiment, at the time of treatment and at the time of observation, it is possible to prevent the affected part from being pulled into the distal opening portion 35*c* by the action force such as suction force acting on the affected part, leading to problems with treatment and observation.

In the present embodiment, the leakage suppression passage portion 80 includes the leakage suppression through-hole 81, and the suction passage portion 90 includes the suction through-hole 91. Thereby, in this embodiment, the above can be implemented with a simple configuration.

In the present embodiment, the leakage suppression through-hole 81 is disposed coaxial with the suction through-hole 91. Thereby, in this embodiment, one of the leakage suppression state and the suction state can easily be switched to the other.

In the meantime, in this embodiment, the suction force is fixed and equal between the leakage suppression state and the suction state. However, the restriction to this is unnecessary. The suction force may be adjusted as desired in accordance with the leakage suppression state and the suction state.

In the present embodiment, the first suction conduit portion 61 may include a filter member, such as a filter, for filtering the fluid, thereby to prevent clogging of the leakage suppression through-hole 81 due to the fluid.

In the present embodiment, it is preferable that the leakage suppression through-hole 81 is larger than the fluid to be sucked.

In the present embodiment, the suction mechanism 50 may be disposed in a direct-viewing endoscope 10. In this case, for example, when the large intestine is inflated, the pressure on the distal opening portion 35*c* side (e.g. the pressure in the large intestine in which the distal end side of the insertion section 20 is inserted) becomes higher than the outside air pressure on the forceps plug portion 36 side. Thereby, like the above, there is concern that the fluid leaks from the forceps plug portion 36. However, the above-described fluid plug unit 70 can suppress such leakage.

[First Modification]

Hereinafter, referring to FIG. 4A and FIG. 4B, a first modification of the present embodiment is described. In the present modification, only different points from the first embodiment are described.

As illustrated in FIG. 4A and FIG. 4B, the leakage suppression passage portion 80 further includes a valve 83 which is provided on a peripheral surface of the piston 73 in a manner to communicate with the first suction conduit portion 61 in the leakage suppression state. The valve 83 opens in the leakage suppression state. Specifically, the valve 83 opens if the pressure on the distal opening portion 35*c* side becomes higher than the outside air pressure on the forceps plug portion 36 side. The pressure on the distal opening portion 35*c* side refers to, for example, the pressure in the large intestine into which the distal end side of the insertion section 20 is inserted.

In this case, the piston 73 of the present modification is formed of, for example, a high-resiliency member of rubber or the like. In addition, the valve 83 includes a slit portion 83*a*. The valve 83 is recessed from the outer peripheral surface toward the inner peripheral surface of the piston 73 so that the valve 83 may easily open.

The valve 83 may be formed such that the surface of the piston 73 is coated with a resin and a slit portion is provided in the resin. The valve 83 may be formed, for example, when the piston 73 is insert-molded. The valve 83 may be provided on the piston 73, for example, by double molding.

Thereby, in the present modification, the structure of the piston 73 can be simplified.

Second Embodiment

Hereinafter, a second embodiment is described with reference to FIG. 5A, FIG. 5B, FIG. 6A and FIG. 6B. In the present embodiment, only different points from the first embodiment are described.

In the present embodiment, the leakage suppression through-hole 81 is not provided, and a gap 85 is provided.

[Configuration]

The leakage suppression passage portion 80 includes a gap 85 which is formed between the inner peripheral surface of the cylinder 71 and the outer peripheral surface of the piston 73, and the internal space of the cylinder 71 (hereinafter referred to as "cylinder internal space portion 711") communicating with the gap 85. The gap 85 is formed between the inner peripheral surface of the cylinder 71 and the outer peripheral surface of the piston 73.

Figure 5A:
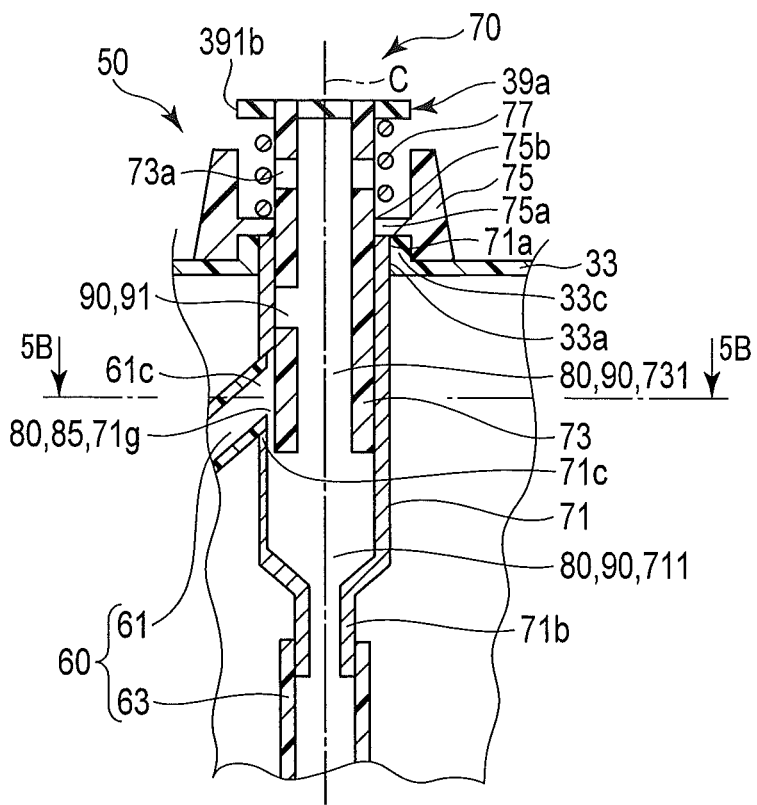
FIG. 5A is a view illustrating an example of a gap in a second embodiment.
Figure 5B:
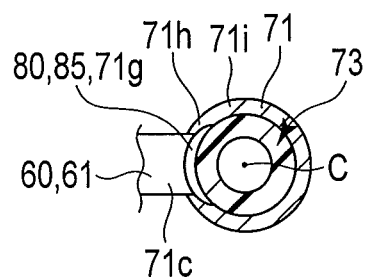
FIG. 5B is a cross-sectional view taken along line 5B-5B in FIG. 5A.

As illustrated in FIG. 5A and FIG. 5B, the gap 85 is formed by an inner peripheral groove 71g provided in the inner peripheral surface of the cylinder 71, such that a portion 71h of the cylinder 71 is smaller in thickness than another portion 71i of the cylinder 71. As illustrated in FIG. 5B, the portion 71h neighbors the portion 71i in a circumferential direction of the cylinder 71, and is provided at the same height position as the portion 71i in the axial direction of the piston 73. The inner peripheral groove 71g is recessed from the inner peripheral surface of the cylinder 71 toward the outer peripheral surface of the cylinder 71. The inner peripheral groove 71g neighbors the side-surface opening portion 71c (first suction conduit portion 61) such that the inner peripheral groove 71g communicates with the first suction conduit portion 61 and cylinder internal space portion 711 in the leakage suppression state and in the suction state. The inner peripheral groove 71g is provided linearly along the axial direction of the cylinder 71. The inner peripheral groove 71g is provided in a part of the cylinder 71 in the circumferential direction of the cylinder 71. In this case, the piston 73 has a uniform thickness.

Here, although the case was described in which the portion 71h of the cylinder 71 is reduced in thickness, the cylinder 71 may be deformed without making the portion 71h smaller in thickness than the portion 71i. Specifically, the cylinder 71 may be deformed so as to be recessed, without being reduced in thickness.

In the meantime, as illustrated in FIG. 6A and FIG. 6B, the gap 85 may be formed by an outer peripheral groove 73g provided in the outer peripheral surface of the piston 73, such that a portion 73h of the piston 73 is smaller in thickness than another portion 73i of the piston 73. As illustrated in FIG. 6B, the portion 73h neighbors the portion 73i in the circumferential direction of the piston 73, and is provided at the same height position as the portion 73i in the axial direction of the piston 73. The outer peripheral groove 73g is recessed from the outer peripheral surface of the piston 73 toward the inner peripheral surface of the piston 73. The outer peripheral groove 73g is disposed below the suction through-hole 91, such that the outer peripheral groove 73g communicates with the first suction conduit portion 61 in the leakage suppression state, does not communicate with the first suction conduit portion 61 in the suction state, and communicates with the cylinder internal space portion 711 in the leakage suppression state and in the suction state. The outer peripheral groove 73g is provided linearly along the axial direction of the piston 73. In this case, the inside diameter of the cylinder 71 is uniform in the range in which the piston 73 slides.

Here, although the case was described in which the portion 73h of the piston 73 is reduced in thickness, the piston 73 may be deformed without making the portion 73h smaller in thickness than the portion 73i. Specifically, the piston 73 may be deformed so as to be recessed, without being reduced in thickness.

Advantageous Effects

Thereby, in the present embodiment, the suction force can be desirably adjusted in the leakage suppression state in accordance with the size of the gap 85.

In the meantime, in the first and second embodiments, the fluid plug unit 70 may be provided not only in the endoscope 10, but also in various insertion devices such as a suction catheter.

The present invention is not limited directly to the above-described embodiments. At the stage of practicing the invention, the structural elements may be modified and embodied without departing from the spirit of the invention. Various inventions may be made by suitably combining a plurality of structural elements disclosed in the embodiments.

What is claimed is:

1. A fluid plug unit for use with a first conduit, a second conduit and a suction device, the first conduit including a distal end and a proximal end and being configured to pass a fluid between the distal end and the proximal end, the second conduit being connected to the suction device, and the suction device being configured to pass the fluid in the first conduit through the fluid plug unit into the second conduit, the fluid plug unit comprising:

a cylinder configured to be connected to the first conduit and to the second conduit such that the first conduit and the second conduit communicate with each other;

a piston fittingly inserted into the cylinder and configured to move in an axial direction of the cylinder, the piston moving between a first position and a second position the piston including an internal space and a vent hole, the internal space communicating with an internal space of the cylinder, and the vent hole being configured to allow the internal space of the piston to communicate with an outside when the piston is in the first position;

the piston having a first passage configured to communicate with the first conduit and the second conduit when the piston is disposed in the first position; and the piston having a second passage configured to communicate with the first conduit and the second conduit when the piston is disposed in the second position;

wherein when the piston is disposed in the first position, outside air flows into the internal space of the cylinder from the vent hole by the suction device, and the fluid is sucked into the second conduit via the first conduit by the suction device;

wherein the first and second passages are configured such that, when the piston is disposed in the first position the fluid flows less easily through the first passage as compared to fluid flow through the second passage when the piston is disposed in the second position.

2. The fluid plug unit according to claim 1, wherein an area of the first passage is smaller than an area of the second passage.

3. The fluid plug unit according to claim 1, wherein an area of the first passage is smaller than an area of the first conduit which communicates with the first passage.

4. A fluid handling system comprising:

the fluid plug unit according to claim 1 and the first conduit, wherein the first conduit includes a forceps plug portion into which a treatment instrument is inserted, and an opening portion from which the treatment instrument projects and which sucks the fluid.

5. The fluid plug unit according to claim 1, wherein the first passage includes a first through-hole configured to penetrate a peripheral surface of the piston and to communicate with the first conduit when the piston is disposed in the first position, and the second passage includes a second through-hole configured to penetrate the peripheral surface of the piston and to communicate with the first conduit when the piston is disposed in the second position.

6. The fluid plug unit according to claim 1, wherein the first passage further includes a valve which is provided on a peripheral surface of the piston in a manner to communicate with the first conduit when the piston is disposed in the first position, the valve being configured to open when the piston is disposed in the first position.

7. The fluid plug unit according to claim 1, wherein the first passage includes a gap formed between an inner peripheral surface of the cylinder and an outer peripheral surface of the piston.

8. The fluid plug unit according to claim 7, wherein the gap is formed by an inner peripheral groove provided in the inner peripheral surface of the cylinder, such that a portion of the cylinder is smaller in thickness than another portion of the cylinder.

9. The fluid plug unit according to claim 7, wherein the gap is formed by an outer peripheral groove provided in the outer peripheral surface of the piston, such that a portion of the piston is smaller in thickness than another portion of the piston.

10. An insertion device comprising:
The fluid plug unit according to claim 1;
an insertion section including the first conduit; and
an operation section connected to the first conduit and the second conduit, the operation section including the fluid plug unit, the operation section being coupled to a proximal end portion of the insertion section, the operation section being configured to operate the insertion section.

11. A fluid handling system comprising:
the fluid plug unit according to claim 1,
the first conduit;
the second conduit; and
the suction device, wherein, when the piston moves to the second position, the fluid is sucked by the suction device via the first conduit and the second conduit.

12. The fluid handling system according to claim 11, wherein the first conduit further includes a forceps plug portion into which a treatment instrument is inserted, the forceps plug portion including an opening from which the treatment instrument projects,
when the position of the piston is moved from the second position to the first position, a transition from a suction state to a leakage suppression state occurs, and when the position of the piston is switched from the first position to the second position, a transition from the leakage suppression state to the suction state occurs, the leakage suppression state being a state in which the fluid at the opening has a higher pressure than an outside air pressure to suppress the fluid from flowing to the outside through the opening of the forceps plug portion, and
the suction state being a state in which, regardless of whether the pressure at the opening is higher than the outside air pressure, the fluid is sucked from the opening and is sucked by the suction device via the first conduit and the second conduit.

13. The fluid plug unit according to claim 1, wherein, when the piston is disposed in the first position, the vent hole is configured to allow the internal space of the piston to communicate with the outside, and
when the piston is disposed in the second position, communication between the outside and the internal space of the piston through the vent hole portion is shut off.

14. A fluid plug unit for use with a first conduit, a second conduit and a suction device, the first conduit a suction device, the first conduit including a distal end and a proximal end and being configured to pass a fluid between the distal end and the proximal end, a the second conduit being connected to the suction device, and the suction device being configured to pass the fluid in the first conduit through the fluid plug unit into the second conduit, the fluid plug unit comprising:
a cylinder configured to be connected to the first conduit and to the second conduit such that the first conduit and the second conduit communicate with each other;
a piston fittingly inserted into the cylinder and configured to move in an axial direction of the cylinder, the piston moving between a first position and a second position, the piston including an internal space and a vent hole, the internal space communicating with an internal space of the cylinder, and the vent hole being configured to allow the internal space of the piston to communicate with an outside when the piston is in the first position;
the piston having a first passage configured to communicate with the first conduit and the second conduit when the piston is disposed in the first position; and
the piston having a second passage configured to communicate with the first conduit and the second conduit when the piston is disposed in the second position;
wherein when the piston is disposed in the first position, outside air flows into the internal space of the cylinder from the vent hole by the suction device, and the fluid is sucked into the second conduit via the first conduit by the suction device;
wherein the first passage includes a first through-hole being configured to penetrate a peripheral surface of the piston and to communicate with the first conduit when the piston is disposed in the first position, and
the second passage includes a second through-hole configured to penetrate the peripheral surface of the piston and to communicate with the first conduit when the piston is disposed in the second position.

15. An insertion device comprising:
the fluid plug unit according to claim 14:
an insertion section including the first conduit; and
an operation section connected to the first conduit and the second conduit, the operation section including the fluid plug unit, the operation section being coupled to a proximal end portion of the insertion section, the operation section being configured to operate the insertion section.

16. fluid handling system comprising:
the fluid plug unit according to claim 14,
the first conduit: the second conduit; and
the suction device, wherein, when the piston moves to the second position, the fluid is sucked by the suction device via the first conduit and the second conduit.

17. The fluid handling system according to claim 16, wherein the first conduit further includes a forceps plug portion into which a treatment instrument is inserted, the forceps plug portion including an opening from which the treatment instrument projects.
when the position of the piston is moved from the second position to the first position, a transition from a suction state to a leakage suppression state occurs, and when the position of the piston is switched from the first position to the second position, a transition from the leakage suppression state to the suction state occurs, the leakage suppression state being a state in which the fluid at the opening has a higher pressure than an outside air pressure to suppress the fluid from flowing to the outside through the opening of the forceps plug portion and the suction state being a state in which, regardless of whether the pressure at the opening is higher than the outside air pressure, the fluid is sucked from the opening and is sucked by the suction device via the first conduit and the second conduit.

18. The fluid plug unit according to claim 14, wherein, when the piston is disposed in the first position, the vent hole is configured to allow the internal space of the piston to communicate with the outside, and when the piston is disposed in the second position, communication between the outside and the internal space of the piston through the vent hole portion is shut off.

* * * * *